Figures 1, 2:
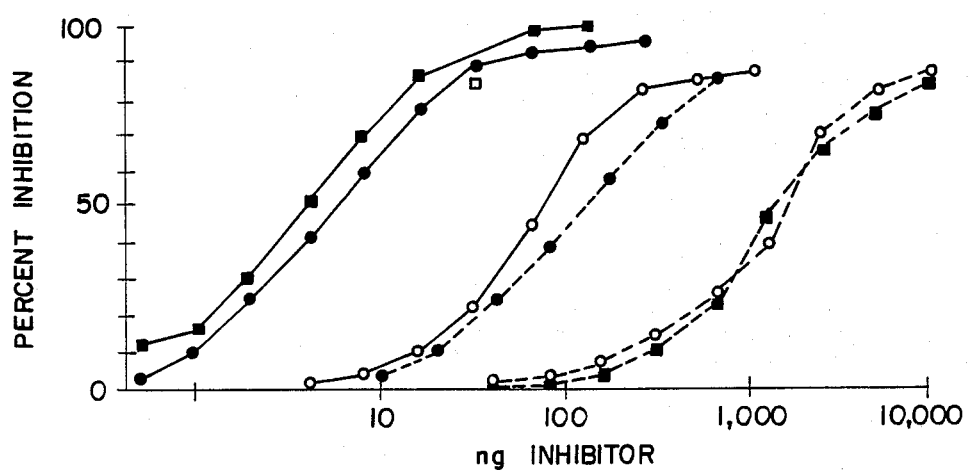

United States Patent [19]

Crawford et al.

[11] Patent Number: 4,873,313
[45] Date of Patent: Oct. 10, 1989

[54] SPECIFIC HYBRIDOMA CELL LINE AND MONOCOLONAL ANTIBODIES PRODUCED FROM SUCH SPECIFIC HYBRIDOMA CELL LINE AND METHOD OF USING SUCH MONOCLONAL ANTIBODIES TO DETECT CARCINOEMBRYONIC ANTIGENS

[75] Inventors: Frances G. Crawford, Houston, Tex.; John E. Shively, Arcadia, Calif.; Charles W. Todd, Arcadia, Calif.; Y. H. Joy Yang, Arcadia, Calif.

[73] Assignee: Beckman Research Institute of City of Hope, Duarte, Calif.

[21] Appl. No.: 725,492

[22] Filed: Apr. 18, 1985

Related U.S. Application Data

[63] Continuation-in-part of Ser. No. 692,515, Jan. 18, 1985, abandoned.

[51] Int. Cl.$^4$ .................... A61K 39/395; C07K 15/14; C12N 15/00; G01N 33/574
[52] U.S. Cl. ......................................... 530/387; 435/7; 435/240.27; 435/172.2; 436/548; 436/538; 436/542; 436/518; 436/527; 436/531; 935/104; 935/106; 935/107; 935/110; 530/395; 530/809; 530/828

[58] Field of Search ................... 435/7, 68, 70, 172.2, 435/240, 241, 948, 240.27; 935/104, 106, 107, 110; 424/1.1, 9, 85; 530/387, 388, 809; 436/518, 527, 531, 548

[56] References Cited

U.S. PATENT DOCUMENTS 4,348,378 9/1982 Goldenberg .......................... 424/1.1
4,359,528 9/1982 Koprowski ........................... 424/1.1
4,467,031 8/1984 Gallati ...................................... 435/7

OTHER PUBLICATIONS

Wagener, C. et al., Journal of Immunology, 130(5):2308–2315 (5–1983).
Wagener, C. et al, Journal of Immunology, 130(5):2302–2307 (5–1985).

Primary Examiner—Howard E. Schain
Assistant Examiner—Jeff P. Kushan
Attorney, Agent, or Firm—Edward S. Irons

[57] ABSTRACT

A specific hybridoma cell line produces monoclonal antibodies which are effective in detecting carcinoembryonic antigens (CEA). The specific hydribome line and monoclonal antibodes are designated as T84.66-A3.1-H11. The monoclonal antibodies are preferably applied to tissues and fluids to detect the degree of binding of such monoclonal antibodies to such carcinoembryonic antigens.

6 Claims, 1 Drawing Sheet

| | COLONIC CAR- CINOMA | GASTRIC CAR- CINOMA | LUNG CAR- CINOMA | MAM- MARY CAR- CINOMA | CO- LONIC POLYP | RE- SEC- TION MARGIN | NORMAL LIVER | GRAN- ULO- GYTES IN BLOOD SMEARS |
|---|---|---|---|---|---|---|---|---|
| CEA. 66-E3 | ++ | ++ | ++ | ++ | + | + | ++ | ++ |
| T84. 1-E3 | ++ | ++ | ++ | ++ | + | + | ++ | ++ |
| CEA. 41C-121-D8 | ++ | ++ | ++ | ++ | + | + | + | ++ |
| T84. 66-A3.1-H-11 | ++ | ++ | ++ | ++ | + | + | − | (W) |
| CEA. 11-H5 | ++ | ++ | ++ | ++ | + | (W) | + | − |

CODE
++   INTENSE STAINING
+    WELL-DEFINED STAINING
(W)  WEAK STAINING
−    NO STAINING

SPECIFIC HYBRIDOMA CELL LINE AND MONOCOLONAL ANTIBODIES PRODUCED FROM SUCH SPECIFIC HYBRIDOMA CELL LINE AND METHOD OF USING SUCH MONOCLONAL ANTIBODIES TO DETECT CARCINOEMBRYONIC ANTIGENS

This application is a continuation-in-part of application Ser. No. 692,515 filed Jan. 18, 1985, now abandoned.

This invention relates to a specific monoclonal antibody which is effective in detecting carcinoembryonic antigens (CEA). The invention also relates to a specific hybridoma cell line which produces such monoclonal antibodies.

Malignant cancers have been recognized as one of the major causes of death in human beings. Furthermore, such emphasis has been placed on various forms of cancer in recent years that there has developed a psychological dread in human beings when the subject of cancer is discussed. In view of the above, a considerable effort has been made in recent years to develop methods and materials which will detect and/or cure various forms of cancer. In spite of such considerable efforts, there has been only limited success in developing such methods and/or materials.

This invention provides a specific hybridoma cell line which produces monoclonal antibodies effective in detecting carcinoembryonic antigens (CEA). The invention also provides the monoclonal antibodies produced from such specific hybridoma cell line. Such monoclonal antibodies are effective in detecting the carcinoembryonic antigens in body fluids and in tissues and in distinguishing between such carcinoembryonic antigens in fluids and tissues and normal antigens in fluids and cell tissues. The monoclonal antibodies may also be used in vivo in detecting carcinoembryonic antigens.

In the drawings:

FIG. 1 is a table showing the binding of different monoclonal antibodies, including the monoclonal antibody of this invention, to various tissue sections and normal granulocytes; and FIG. 2 illustrates the binding of various monoclonal antibodies to a radioactive carcinoembryonic antigen inhibitor in the presence of carcinoembryonic antigens and non-carcinoembryonic antigens.

Two publications specify the hybridoma cell line and monoclonal antibodies constituting this invention, the methods of producing such hybridoma cell line and monoclonal antibodies and the effectiveness and advantages of such hybridoma cell line and monoclonal antibodies in detecting carcinoembryonic antigens. These publications are identified as follows:

1. An article entitled "Monoclonal Antibodies for Carcinoembryonic Antigen and Related Antigens as a Model System: A Systematic Approach for the Determination of Epitope Specifities of Monoclonal Antibodies" by Christoph Wagener, Y. H. Joy Yang, Frances G. Crawford and John E. Shively. This article was published at pages 2308–2315 of Vol. 130, No. 5 of the Journal of Immunology in May, 1983.

2. An article entitled "Monoclonal Antibodies for Carcinoembryonic Antigen and Related Antigens As a Model System: Determination of Affinities and Specifities of Monoclonal Antibodies by Using Biotin-Labeled Antibodies and Avidin as Precipitating Agent in a Solution Phase Immunoassay" by Christoph Wagener, Brian R. Clark, Karen J. Rickard and John E. Shively. This article was published at pages 2302–2307 of Vol. 130, No. 5, of the Journal of Immunology in May, 1983.

Although the two (2) articles specified above are complete in many respects, they identify the hybridoma cell line of this invention only as "T84.66-A3.1-H11". Such an identification does not constitute a sufficient disclosure of the hybridoma cell line of this invention to provide a public disclosure of such a cell line. This is particularly true since only applicants' assignee and a licensee of applicants' cell line have cells from such hybridoma cell line and monoclonal antibodies developed from such cells. This licensee has rights from applicants' assignee to market applicant's cell line and monoclonal antibodies developed from such cells to detect carcinoembryonic antigens (CEA).

Through their assignee of record in this application, applicant deposited cells from the hybridoma cell line T84.66-A3.1-H11 and monoclonal antibodies developed from such hybridoma cell line with the American Type Culture Collection, at 12301 Parklawn Drive, Rockville, Md. 20852. These cells were accepted by the American Type Culture Collection on Mar. 1, 1985, after the American Type Culture Collection tested samples of such cells. Such deposit of such cells has been identified by the American Type Culture Collection by the designation HB8747. The cells were deposited by applicants' assignee with the American Type Culture Collection with the understanding that samples of such cells would be released to third parties only after applicant's assignee obtained a patent on such cells and the monoclonal antibodies developed from such cells.

Cell lines and media. Parent mouse myeloma cell line Sp2/0-Ag 14 was obtained from the Cell Distribution Center at the Salk Institute, San Diego, Calif. Hybrid and myeloma lines were maintained in Dulbecco's modified Eagle medium (DMEM; GiBCO, Grand Island, N.Y.) supplemented with 10% to 20% heat-inactivated fetal calf serum (GiBCO), $10^{-5}$M 2-mercaptoethanol, 0.01M HEPES[5] buffer, pH 7.4, 100 U/ml penicillin, 100 μg/mi streptomycin, 0.25 μg/ml Fungizone (GlBCO), and, occasionally, 100 μg/ml gentamicin sulfate (Microbiological Associates). The human colorectal carcinoma cell line HC 84S, provided by H. Murakami and G. Sato, was grown in a 1:1 mixture of DMEM and Ham's F12 medium (Irvine Scientific, Irvine, Calif.) supplemented with 2.5% fetal calf serum, 8% heat-inactivated horse serum, 0.12% $NaHCO_3$, 90 U/ml penicillin, 90 μg/ml streptomycin, 8 μg/ml ampicillin, and 2 mM glutamine.

Immunization. The CEA preparation used as immunogen was purified as described by J. E. Coligan, J. T. Lautenschlegar, M. L. Egan and C. W. Todd in an article entitled "Isolation and Characterization of Carcinoembryonic Antigen" and published in 1972 in Immunochemistry at Vol. 9, page 377, and by D. G. Pritchard and C. W. Todd in an article entitled "Purification of Carcinoembryonic Antigen by Removal of Contaminating Mucopolysaccharides" and published in 1976 in Cancer Research at Vol. 36, page 4699. Female BALB/c mice (12 weeks old) were injected subcutaneously with 25 μg CEA in about 100 μl complete Freund's adjuvant and boosted subcutaneously after 4 weeks with the same amount of CEA in 100 μl incomplete Freund's adjuvant. Four weeks later and 72 hr. before fusion, 10 μg CEA in 20 μl of 0.14M NaCl solution were injected intraveneously. Alternatively, $10^7$ HC84S cells were harvested, washed and resuspended in 0.14M NaCl solution and were injected intravenously and boosted once with the same cells 4 weeks later and 72 hours before fusion. The antibodies induced against the transplanted colonic carcinoma cells were designated T84, the designation originally used for the transplanted cell line as specified by H. Murakami and H. Masui in an article entitled "Hormonal Control of Human Color Carcinoma Cell Growth in Serum-Free Medium" and published in 1980 in The Proceedings of the National Academy of Sciences of the United States of America at Vol. 77, page 3464.

Cell fusion, cloning and growth of tumors in mouse. Cell fusion was performed as described by Y. H. J. Yang, F. C. Grumet, B. Fendly, E. Engleman and J. E. Shively in an article entitled "Protein: A Binding Assay for the Identification of HLA Antigens on Peripheral Blood Leucocytes by Monoclonal Antibodies: Application to HLA B27" and published in 1982 in Hybridoma at Vol. 1, page 243. Briefly, splenocytes and myeloma cells (3:1) were exposed to $\mu$1 ml of 50% polyethylene glycol in DMEM at 37° C. for 1 min. The polyethylene glycol was diluted by an additional 21 ml of DMEM. The fused cells were resuspended in DMEM plus 20% fetal calf serum and distributed into three 96-well cluster plates (Costar 3596) with $10^5$ normal spleen cells. Cluster plates were incubated in a humidified 7% $CO_2$ atmosphere at 37° C. overnight, followed by the addition of 0.1 ml of hypoxanthine-aminopterin-thymidine (HAT) medium to each well for selection. All of the supernatants were screened for antibody production after 2 weeks of culture. Cloning under limiting dilution was carried out by using 15% spent medium from the parent line. The cloned hybrid cells (4 to $5 \times 10^6$) were implanted in BALB/c mice intraperitoneally. Sera and ascites fluids were collected from mice after 10 to 14 days.

Antibody detection assays. Culture supernatants were screened for anti-CEA antibody by a solid-phase enzyme immunoassay. Polyvinyl chloride microtiter plates with 96 wells were coated with CEA at a concentration of 2 $\mu$g/ml in 0.2M carbonate buffer, pH 9.4, by using 100 $\mu$l per well. The dishes were coated overnight at room temperature or for 4 hours at 37° C. The CEA solution was reused twice for coating before discarding. The following incubation steps were performed at 37° C. After blocking unspecific binding sites of the wells with 200 $\mu$l phosphate-buffered saline, pH 7.2 (PBS) containing 1% BSA (PBS-BSA) for 2 hours, 50 $\mu$l of the undiluted supernatants were added to the respective wells (1.5 hours), followed by 100 $\mu$l of a 1/500 dilution of goat anti-mouse IgG antibody, conjugated to alkaline phosphatase (Tago, Burlingame, Calif.) in PBS containing 5 mg/ml BSA and 2% fetal calf serum (1.5 hr). After washing the wells with 0.05M ethanolamine-buffered saline, pH 9.5, the wells were incubated with 100 $\mu$l of a solution containing 0.4 mg p-nitrophenyl phosphate (Sigma, St. Louis, MO) per milliliter of ethanolamine-buffered saline. After 1 hour, the reaction was terminated by the addition of 3M NaOH (20 $\mu$l/well). The positive wells were identified either visually or by measuring the OD at 405 nm. The CEA binding of the culture supernatants showing a positive result in the enzyme immunoassay was tested by radioimmunoassay, with rabbit anti-mouse IgG serum used as a second antibody source. Briefly, 1 ng $^{125}$I-CEA ($4.0 \times 10^4$ cpm) was incubated with 200 $\mu$l of culture supernatant and 1 to 3 $\mu$g mouse IgG in the presence of $^{57}$Co ($10^4$ cpm) as a volume marker in PBS overnight. The antigen-antibody complex was precipitated by 25 $\mu$l of rabbit anti-mouse IgG serum at 37° C. for 1 hr. The resulting precipitates were cooled and centrifuged and radioactivity was determined in a Beckman gamma counter. The precipitates containing more than 10,000 cpm were washed and separated into component bands on an SDS-polyacrylamide slab gel (20). The $^{125}$I-CEA bands were located by autoradiography on x-ray film.

Isotype determination. The isotypes of the immunoglobulin from hybrid culture fluids and of the purified mouse IgG were determined by using modifications of the antibody detection assay described above. The subclasses of heavy chains were determined as follows. After addition of appropriate dilutions in PBS-BSA of the culture fluids or purified IgG, respectively, to the CEA-coated wells, 100 $\mu$l of a 1/1000 dilution in PBS-BSA of goat antiserum specific for mouse IgG1, IgG2a, and IgG2b (Meloy, Springfield, VA) was added (37° C., 90 min), followed by addition of 100 $\mu$l of a 1/1000 dilution in PBS (containing 5 mg BSA/ml and 2% fetal calf serum) or rabbit anti-goat IgG antibody, conjugated to alkaline phosphatase (Miles Laboratories, Elkhart, IN) (37° C., 90 minutes). Addition of substrate and termination of the reaction were performed as described above. The subclasses of the IgG heavy chains in the ascites fluids were also determined by eluting the IgG bound to protein A-Sepharose CL-4B (Sigma) at different Ph values as described by P. L. Ely, S. J. Prowse and C. R. Jenkin in an article entitled "Isolating of Pure $IgG_1$ $IgG_{2a}$ and $IgG_{2b}$ Immunoglobulins from Mouse Serum Using Protein A-Sepharose" and published in 1978 in Immunochemistry at Vol. 15, page 429. For the determination of light chain isotypes, the goat antisera specific for mouse IgG subclasses were replaced by rabbit antisera specific for mouse $\lambda$- and $\kappa$-chains (Miles Laboratories, Elkhart, IN). Goat anti-rabbit IgG antibody conjugated to alkaline phosphatase (Miles) was used in the subsequent incubation step. Monoclonal antibody from the hybridoma T84.66-A3.1-H11 was found to have Kappa(K)-light chains and IgG-1 heavy chains.

Purification of IgG. IgG was purified from mouse ascites fluid (MAF) by the use of protein A-Sepharose CL-4B (Sigma) according to the article published by Ey et al. in Immunochemistry in 1980. MAF (1 to 2 ml) was applied to a gel volume of 5 ml. The purity of the IgG fractions was determined by SDS polyacrylamide slab gel electrophoresis by using the method described by V. K. Laemmli in "Cleavage of Structural Proteins during the Assembly of the Head of Bacteriophage T4" published in 1970 in Nature in Vol. 227, pages 680. The concentration of polyacrylamide was 12%. The purified monoclonal antibody from the hybridoma cell line T84.66-A3.1-H11 was shown to contain only heavy and light chains by the analysis, a result consistent with a purified IgG.

Protein concentration. Protein concentrations of purified immunoglobulins were calculated from the absorbance of the solutions at 280 nm, assuming an extinction coefficient (1% w/v; 1 cm) of 14.2.

Isoelectrofocusing. Horizontal flatbed isoelectrofocusing of the IgG fractions purified from MAF was performed on a Bio-Rad 1415 electrophoresis cell (Bio-Rad, Richmond, Calif.). The IgG fractions were dialized against water and lyophilized. Immediately before use, the IgG fractions were dissolved in O'Farrell's lysis buffer to give a final concentration of 2 mg/ml. The gels were mixed as follows: 4.85% acrylamide, 0.15% bis-acrylamide, 5% glycerol, 2% ampholines (1.13% Bio-Lyte, pH 6-8, 0.77% Bio-Lyte, pH 4-6, 0.1% Bio-Lyte, pH 3-10; Bio-Rad), 8M urea, $9.7 \times 10^{-6}$ riboflavin-5'-phosphate, and 0.01% ammonium persulfate. The polymerized gel was run at a constant power of 7 W, with 700 V initially, rising to 1800 V after 2.5 hr. After a pre-run of 30 minutes, 5 µl of the sample were applied to the gel by using Teflon sample applicators. The samples were run for 2 hr. Fixation and staining of gels was performed as described by P. H. O'Farrell in an artiacle entitled "High Resolution Two-Dimensional Electrophoresis of Proteins" in 1975 in the Journal of Biological Chemistry (Vol. 250, page 4007). The results of the analysis confirm that the antibody is monoclonal (one species) as expected for a cloned hybridoma cell line.

Determination of epitope specificity. Monoclonal IgG was isolated on a protein A-Sepharose column and labeled with $^{125}$I by the chloramine-T method described by W. M. Hunter and F. C. Greenwold in "Preparation of Iodine-131 Labelled Human Growth Hormone of High Specific Activity" in 1962 in Nature (vol. 194, page 495). A constant volume of 50 µl of labeled antibody was added to 100 µl of doubling dilutions of cold antibody. Fifty microliters of each dilution were added to the wells of a 96-well polyvinyl chloride microtiter dish previously coated with native CEA or CEA deglycosylated in accordance with procedures described by J. N. Glassman, C. W. Todd and J. E. Shively in an article entitled "Chemical Deglycosylation of Carcinoembryonic Antigen for Amino and Sequence Studies" and published in 1978 in Biocham. Biophys. Res. Commun. at Vol. 85, page 209. The final amount of unlabeled IgG per well was 0.5 to 1120 ng. The labeled material corresponded to 20,000 to 100,000 cpm/well. After an incubation time of 2 to 3 hr at 37° C., the plates were washed five times with PBS, and the wells were cut and counted in a gamma scintillation counter. In addition to the purified monoclonal antibodies, MAF and culture supernatants from different clones were tested in a competition assay for CEA binding against five radiolabeled monoclonal antibodies. Seventy-five microliters of a 1/100 dilution in PBS-BSA of ascites fluid were mixed with an equal volume of labeled antibody. Fifty microliters of this solution were added to the respective wells previously coated with CEA. The culture fluids were mixed with the labeled antibodies without prior dilution. Inhibition of binding was expressed as a percentage of the binding of labeled antibodies in the absence of unlabeled antobodies. The completion for CEA binding of the culture supernatants 2 weeks after fusion but before cloning was investigated by using a modification of the procedure described above. The wells were coated with CEA as described. The wells were then incubated with 100 µl of undiluted culture fluid for 2 hours at 37° C., followed by 50 µl per well of labeled antibody for 1.5 hour at 37° C. After washing the plates, the wells were counted as described. The epitope specificity testing revealed that the T84.66-A3.1-H11 monoclonal antibody recognizes a unique, single epitope in CEA, and that the epitope is of a protein, not carbohydrate nature.

Immunohistochemical staining. In the following tissues, the binding of monoclonal anti-CEA antibodies was investigated: well-differentiated colonic adenocarcinoma, moderately differentiated gastric adenocarcinoma, poorly differentiated squamous cell carcinoma of the lung, poorly differentiated ductal carcinoma of the breast, benign colonic polyp, resection margin of a colonic carcinoma, normal liver and peripheral blood smears.

For the localization of antigens reacting with the monoclonal anti-CEA antibodies, a modification of the avidin-biotin-peroxidase complex technique was applied, as described by M. Hsu, L. Raine and H. Fanger in an article entitled "Comparative Study of the Perioxidase—Angiperoxidase Method and Av Avidin-Biotin Complex Method for Studying Polypeptide Hormones with Radioimmunoassay Antibodies" and published in 1981 in the American Journal of Clinical Pathology (Vol. 75, page 734). Tissues fixed in 10% buffered formaldehyde and peripheral blood smears fixed in 95% ethanol for 20 minutes were used. The tissue sections were deparaffinized and hydrated via a series of xylene and graded ethyl alcohol rinses. Endogenous peroxidase was blocked by 0.5% $H_2O_2$ in methanol (20 minutes). PBS was used as a washing solution and as a diluent for the avidin-biotin-peroxidase-complex (ABC reagent, Vector Laboratories, Burlingame, Calif.). The monoclonal anti-CEA antibodies, normal mouse IgG (Pel Freez Biologicals, Rogers, AR) and the biotin-labeled IgG fraction of horse anti-mouse IgG antiserum (Vector Laboratories) were diluted in PBS containing 10% normal goat serum. The monoclonal antibodies and the normal mouse IgG were applied to the tissue sections at at a final concentration of 1.52 µg/ml. For the blood smears, a final concentration of 7.6 µg/ml was used. The biotin-labeled IgG fraction of horse anti-mouse IgG anti serum was diluted 1/100, the avidin-biotin-peroxidase complex was diluted 1/40. The staining solution was made up by diluting 0.24% 3-amino-9-ethylcarbazole in dimethyformamide 1/10 in 0.2M acetate buffer, pH 5.2, which contained 0.012% hydrogen peroxide (26). The staining procedure after the blocking of endogenous peroxidase was as follows: (1) $3 \times$ PBS, 20 minutes; (2) undiluted normal goat serum, 20 minutes) (3) excess serum blotted from slides; (4) monoclonal anti-CEA antibodies or normal mouse IgG; tissue sections: 20 to 24 hours; blood smears: 1 hours; (5) $3 \times$ PBS, 5 minutes; (6) undiluted normal goat serum, 20 minutes); (7) excess serum blotted from slides; (8) biotin-labeled horse anti-mouse IgG antibody, 20 minutes; (9) $3 \times$ PBS, 5 minutes; (10) ABC reagent, 20 minutes; (11) $3 \times$ PBS, 5 minutes; (12) staining solution, 10 minutes; (13) $3 \times$ PBS. For each tissue specimen or blood sample, a negative control was performed, with the use of normal mouse IgG instead of the monoclonal antibodies. Some of the positive slides as well as the negative controls were counterstained with hematoxylin. The tissue section and blood smears were mounted in Aqua Mount (Lerner Laboratories, New Haven, CT).

FIG. 1 is a table which specifies monoclonal antibodies with different epitope specifities in the first column and which specifies the strength of binding of such monoclonal antibodies to various tissue sections and normal granulocytes. This is indicated by a code in which an indication of (++) indicates intense staining, a code of (+) indicates well-defined staining, a code of (W) indicates weak staining and a code of (−) indicates no staining. As indicated in the successive columns of FIG. 1, the binding of the different monoclonal antibodies was attempted to (1) well-differentiated colonic adenocarcinoma, (2) moderately differentiated gastric adenocarcinoma, (3) poorly differentiated squamous cell carcinoma of the lung, (4) poorly differentiated ductal carcinoma of the breast, (5) benign colonic polyp, (6) resection margin of a colonic carcinoma, (7) normal liver and (8) peripheral blood smears.

As will be seen from the table constituting FIG. 1, all of the different monoclonal antibodies specified in FIG. 1 exhibited strong bonds to all of the different carcinoma specified in FIG. 1. Furthermore, all of the different monoclonal antibodies in FIG. 1 exhibited a well-defined bond to colonic polyps. In resection margins of a colonic carcinoma where the occurrence of a carcinoembryonic antigen has been found by some authors but questioned by others, a well-defined binding occurred to all of the monoclonal antibodies specified in FIG. 1 except that a weak binding occurred to the monoclonal antibody identified as CEA 11-H5. However, the monoclonal antibody identified as T84.66-A3.1-H11 is the only antibody which exhibits no binding to a normal liver and only a weak binding to granulocytes in blood smears. In these respects, the monoclonal antibody identified as T84.66-A3.1-H11 is superior to the monoclonal antibody identified as CEA.11-H5 since this monoclonal antibody has a well defined binding to a normal liver.

FIG. 2 sets forth curves comparing the inhibition in the binding of ratio labeled carcinoembryonic antigen to three different monoclonal antibodies (one of these being the monoclonal antibody of this invention). In FIG. 2, caarcinoembryonic antigen (CEA) and tumor-extracted CEA related antigen were used as inhibitors. The response curves involving the use of carcinoembryonic antigen (CEA) as the inhibitor are illustrated in FIG. 2 by long dash lines and the response curves involving the use of tumor-extracted CEA related antigens as the inhibitor are illustrated in FIG. 2 by short dash lines.

The curves in FIG. 2 involving the use of the monoclonal antibody T84.66-A3.1-H11 were obtained by using 0.9 nanograms of IgG per tube. These curves are identified in FIG. 2 by plot points having a solid rectangle. The curves involving, in FIG. 2, the use of the monoclonal antibody T84.1-E3 were obtained by using 1.4 nanograms of IgG per tube. These curves are identified in FIG. 2 by plot points having a hollow circle. The curves involving in FIG. 2 the use of the monoclonal antibody CEA.66-E-3 were obtained by using 26.5 nanograms of IgG per tube. These curves are identified in FIG. 2 by plot points having a solid circle.

As will be seen in FIG. 2, the abscissa indicates the amount in nanograms of the particular one of the inhibitors required to produce a percentage of inhibition such as indicated along the ordinate. The most sensitive inhibition occurs when the carcinoembryonic antigen is used as the inhibitor and the monoclonal antibody T84.66-A3.1-H11 is attempted to be bound to the carcinoembryonic antigen radiolabeled as with $^{125}I$ (iodine). The least sensitive inhibition occurs when the tumor-extracted CEA-related antigen i used as the inhibitor and it is attempted to bind the monoclonal antibody T84.66-A3.1-H11 is attmpted to be bound to the radiolabeled carcinoembryonic antigen. This establishes that the monoclonal antibody T84.66-A3.1-H11 has a considerably greater difference between its binding to the carcinoembryonic antigen and a non-carcinoembryonic antigen than any of the other monoclonal antibodies.

The degree in the difference between the binding of the monoclonal antibody T84.66-A3.1-H11 on the one hand and the binding of the monoclonal antibodies T84.1-E3 and CEA.66-E3 on the other hand may be seen from certain comparisons obtained from FIG. 2. For example, approximately a 23-fold greater amount of tumor-extracted CEA-related antigen was needed to achieve a binding inhibition of 50% for each of monoclonal antibodies T84.1-E3 and CEA.66-E3 than the amount needed when carcinoembryonic antigen (CEA) was used. In contrast, approximately a 351-fold greater amount of tumor-extracted CEA-related antigen was needed to achieve a binding inhibition of 50% for the monoclonal antibody T84.66-A3.1-H11 than the amount needed when carcinoembryonic antigen (CEA) was used.

Tests have determined that the affinity constant of the monoclonal antibody T84.66-A3.1-H11 for the carcinoembryonic antigen is in the order of $2.6 \times 10^{10} M - 1$ for an inhibition curve. This affinity constant has been determined in accordance with modifications in a method disclosed by R. Muller in an article entitled "Calculation of Average Antibody Affinity in Anti-Hapten Sera from Data Obtained by Competitive Radioimmunoassay" and published in the Journal of Immunological Methods in 1980 in Volume 34, page 345.

The monoclonal antibody T84.66-A3.-H11 is included in a kit which has been approved by the Food and Drug Administration of the United States Government for use in detecting carcinoembryonic antigens in body fluids of human beings. This kit has been developed by Hoffmann-La Roche Inc. of Nutley, N.J. The monoclonal antibody T84.66-A3.1-H11 is being licensed by applicant's assignee to Hoffmann-La Roche for use in such kits.

The discussion above also indicates that the monoclonal antibody T84.66-A3.1-H11 has been used to detect, and is effective in detecting, carcinoembryonic antigen in tissues. The monoclonal antibody T84.66-A3.1-H11 can also be used in detecting carcinoembryonic antigen in vivo, particularly when the monoclonal antibody is radiolabeled.

Although this invention has been disclosed and illustrated with reference to particular embodiment, the principles involved are susceptible for use in numerous other embodiments which will be apparent to persons skilled in the art. The invention is, therefore, to be limited only as indicated by the scope of the appended claims.

We claim:

1. A hybriboma cell line designated as T84.66-A3.1-H-11 cell line ATCC Accession No. HB8747.

2. Monoclonal antibodies designated as T84.66-A3.1-H11 antibodies ATCC Accession No. HB8747.

3. A method of detecting carcinoembryonic antigens including the steps of applying, to such carcinoembryonic antigens, monoclonal antibodies designated as T84.66-A3.1-H11, ATCC Accession No. HB8747 and detecting the degree of binding of such monoclonal antibodies to the carcinoembryonic antigens.

4. A method as set forth in claim 3 wherein
   the monoclonal antibodies T84.66-A3.1-H11, ATCC Accession No. HB8747 are applied to body fluids containing the carcinoembryonic antigens to detect the degree of binding of such monoclonal antibodies to such carcinoembryonic antigens.

5. A method as set forth in claim 3 wherein
   the monoclonal antibodies T84.66-A3.1-H11, ATCC Accession No. HB8747 are applied to tissues containing the carcinoembryonic antigens to detect the degree of binding of such monoclonal antibodies to such carcinoembryonic antigens.

6. In a method of detecting carcinoembryonic antigens in an individual,
applying monoclonal antibodies T84.66-A3.1-H11, ATCC Accession No. HB8747 to tissues or fluids of the individual, and detecting the degree of binding of such monoclonal antibodies to antigens in such tissues or fluids.

* * * * *

UNITED STATES PATENT AND TRADEMARK OFFICE
CERTIFICATE OF CORRECTION

PATENT NO. : 4,873,313

DATED : October 10, 1989

INVENTOR(S) : Frances G. Crawford, John E. Shively, Charles W. Todd and H. Joy Yang It is certified that error appears in the above-identified patent and that said Letters Patent is hereby corrected as shown below:

ON THE TITLE PAGE:

Column 1, line 9, after the title, insert:

--This invention was made with government support under Grant No. CA37808 awarded by the National Institutes of Health. The government has certain rights in the invention.--

Signed and Sealed this

Ninth Day of February, 1993

Attest:

STEPHEN G. KUNIN

Attesting Officer

Acting Commissioner of Patents and Trademarks